United States Patent [19]

Singh-Verma et al.

[11] Patent Number: 4,865,757

[45] Date of Patent: Sep. 12, 1989

[54] PERSONAL HYGIENE PREPARATION COMPRISING SOAP AND ETHER CARBOXYLATES

[75] Inventors: Shyam B. Singh-Verma, Kerpen-Türnich; Josef Jordan, Kerpen; Raimund Sossna, Cologne, all of Fed. Rep. of Germany

[73] Assignee: Eau de Cologne- & Parfümerie-Fabrik, Cologne, Fed. Rep. of Germany

[21] Appl. No.: 150,531

[22] Filed: Jan. 29, 1988

[30] Foreign Application Priority Data

Feb. 4, 1987 [DE] Fed. Rep. of Germany ....... 3703258

[51] Int. Cl.$^4$ .......................... C11D 1/06; C11D 9/30; C11D 10/04
[52] U.S. Cl. .................................... 252/117; 252/108; 252/132; 252/134; 252/DIG. 14; 252/546; 252/DIG. 16; 252/DIG. 5
[58] Field of Search .................. 252/174.22, DIG. 16, 252/DIG. 5, 546, 547, 117

[56] References Cited

U.S. PATENT DOCUMENTS

| | | | |
|---|---|---|---|
| 3,988,438 | 10/1976 | Weinstein | 424/70 |
| 4,130,497 | 12/1978 | Oneto et al. | 252/132 |
| 4,223,163 | 9/1980 | Guilloty | 568/618 |
| 4,285,826 | 8/1981 | Bertozzi et al. | 252/117 |
| 4,664,835 | 5/1987 | Grollier | 252/90 |
| 4,783,282 | 11/1988 | Smid | 252/546 |

FOREIGN PATENT DOCUMENTS

| | | |
|---|---|---|
| 582065 | 8/1959 | Canada . |
| 102118 | 3/1984 | European Pat. Off. . |
| 154380 | 9/1985 | European Pat. Off. . |
| 1169496 | 4/1967 | United Kingdom . |
| 1284791 | 8/1972 | United Kingdom . |

*Primary Examiner*—Prince E. Willis
*Attorney, Agent, or Firm*—Spencer & Frank

[57] ABSTRACT

A personal hygiene preparation, containing: soap; a coloring agent, fragrance, skin care substance, or conditioner; and at least one synthetic detergent. The synthetic detergent is a carboxymethyl ether of an ethoxylated fatty acid, a carboxymethyl ether of an ethoxylated fatty acid amide, or a carboxymethyl ether of an ethoxylated fatty alcohol, and their salts, and mixtures thereof.

6 Claims, No Drawings

PERSONAL HYGIENE PREPARATION COMPRISING SOAP AND ETHER CARBOXYLATES

BACKGROUND OF THE INVENTION

The present invention relates to a personal hygiene preparation based on the alkali salts of at least one given fatty acid (soap) as the cleansing substance with added dyestuffs and/or fragrance and/or skin care substances and/or conditioners.

When cleaning the skin with a personal hygiene preparation based on soap, i.e. based on the alkali salts of certain fatty acids, the skin is freed of skin tallow accumulations, dirt and the remainders of previously applied cosmetics, such as powder, creams or the like. A conventional soap has considerable drawbacks with respect to skin physiology, particularly for sensitive skin. For example, soap attacks the natural hydrolipid coat of the skin. The acid-protection coating of the skin is destroyed by the alkali in the soap so that even with intensive rinsing with water, the natural state is reproduced only after about 1 to 1.5 hours. Moreover, washing with soap results in considerable swelling of the skin which is of subordinate significance for healthy skin but may lead to drying or chapping, i.e. so-called "rough" skin, in tired, sensitive or diseased skin affected, for example, by eczema, acne or the like.

To overcome these drawbacks, synthetic cleansing substances, so-called syndets [synthetic detergents], have also been used as personal hygiene preparations. They have good foaming ability, and cleansing power greater than soap. Since swelling of the skin is avoided, these syndets are particularly suitable for the cleansing of tired, sensitive or diseased skin. These advantages over a conventional soap are opposed by some disadvantages: for example, skin tallow is removed from the skin which again may lead to drying and chapping. Additionally, the natural flora of the skin is interfered with to a great extent. Therefore, it is generally necessary to add refattening substances to such syndets.

SUMMARY OF THE INVENTION

It is now an object of the invention to provide a personal hygiene preparation based on soap, i.e. based on the alkali salts of certain fatty acids, which has substantially improved skin-physiology characteristics.

This is accomplished by a personal hygiene preparation, containing: soap; a coloring agent, fragrance, skin care substance, or conditioner; and at least one synthetic detergent. The synthetic detergent is a carboxymethyl ether of an ethoxylated fatty acid, a carboxymethyl ether of an ethoxylated fatty acid amide, or a carboxymethyl ether of an ethoxylated fatty alcohol, and their salts and mixtures thereof. Surprisingly, it has been found that even the addition of a relatively small quantity of the syndet suppresses the drawbacks of the two components and results in better compatibility with the skin.

DESCRIPTION OF THE PREFERRED EMBODIMENTS

According to one embodiment of the invention, it is provided that the mixing ratio between soap and syndet lies in a weight percent range from 92:3 to 65:30. The remainder to make up 100% consists of the customary additives for personal hygiene preparations as mentioned above. Preferably, a mixing ratio in a range from 90:5 to 70:25, particularly in a range from 85:10 to 75:20 is provided for this purpose.

In another embodiment of the invention, a flowable consistency, i.e. a liquid, is realized with a total content of cleansing substances from 15 to 40 weight percent and a pasty consistency is realized with a total content of cleansing substances from 30 to 80 weight percent with respect to the total weight.

In another embodiment, a bar-type consistency is realized with a total content of cleansing substances of at least 80 weight percent with respect to the total weight.

Another embodiment is exemplified in that syndets in the form of the alkali salts of at least one carboxymethyl ether of certain ehoxylated fatty acid amides or fatty acids or fatty alcohols may be combined with the soap. This mixture results in a personal hygiene preparation which combines the advantages of the two components in an excellent manner. It is distinguished by a particularly creamy and stable foam and by an especially pleasant feeling on the skin during the washing process itself as well as after rinsing and drying. The skin is subjected to less stress since swelling and removal of skin tallow from the skin are reduced considerably. As a whole, a pleasant feeling results after use which is identified in a previously unknown manner as extremely mild and friendly to the skin. It has also been found that, particularly compared to conventional, pure soap bars, any fragrance added become clearly noticeable so that the quantity of aromatics to be added can be reduced considerably. Yet, in a bar of the personal hygiene preparation according to the invention, the fragrance effect remains in effect a long time after use. Moreover, cracks in bar-type preparations are completely prevented. Even the formation of calcium soaps, the cause of rings around washbasins or bathtubs, are prevented or reduced considerably.

In another embodiment of the invention it is provided that the monoethanolamine, diethanolamine or triethanolamine salts are used instead of the alkali salt of at least one carboxymethyl ether of certain ethoxylated fatty acid amides or fatty acids or fatty alcohols. The syndets employed advisably exhibit a degree of ethoxylation between 2 and 20, so that the fatty acid, fatty amide, or fatty alcohol is substituted with between 2 and 20 ethoxy groups. Suitable fatty acids or fatty acid amides or fatty alcohols used as syndets for all embodiments of the invention are, in particular, lauric acid, myristic acid, palmitic acid, stearic acid and oleic acid and their amides or alcohols as well as mixtures thereof.

Preferably, only one class of syndets is mixed with the soap since then the mutually positive influence of the components is most favorable. The use of two or more different syndets may have the result that they have a negative influence on one another with respect to their compatibility, skin-physiology effect as well as with respect to their processability. The particular advantage of the stated classes of syndets is, in particular, that the effect of the soap, on the one hand, and of the syndet, on the other hand, positively influence one another to result in the above-discussed advantages.

If one attempts, however, to mix soaps with conventional syndets, such as benzyl sulfonates, fattyacid ether sulfates, fatty acid sulfosuccinates or cleansing substances of a chemically similar structure, these mixtures, due to their consistency, cannot be processed into cosmetically satisfactory preparations. Moreover, they do not have the desired good skin-physiology effects.

The present disclosure relates to the subject matter disclosed in the Federal Republic of Germany, No. P 37 03 258.5, on Feb. 4th, 1987, the entire specification of which is incorporated herein by reference.

It will be understood that the above description of the present invention is susceptible to various modifications, changes and adaptations, and the same are intended to be comprehended within the meaning and range of equivalents of the appended claims.

General structural formulas of anionics mentioned in the appended claims are as follows:

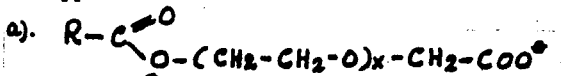

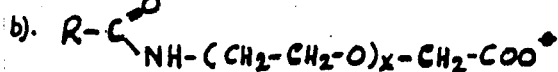

$X = 2-20$ $R = C_7-C_{17}$-Alkylgroups derived from coconut fatty acids

What is claimed is:

1. A personal hygiene preparation, comprising:
   soap, consisting of an alkali salt of at least one fatty acid;
   a least one material selected from the group consisting of dyestuff, fragrance, skin care substances and skin conditioners; and
   at least one synthetic detergent comprising at least one selected from the group consisting of a carboxymethyl ether of an ethoxylated fatty acid and a carboxymethyl ether of an ethyloxylated fatty acid amide, wherein the ratio between the soap and the synthetic detergent is in a weight percent range from about 90:5 to about 70:25.

2. A personal hygiene product as defined in claim 1, wherein the soap and synthetic detergent comprise from about 15 to about 40 weight percent of the total weight of said preparation.

3. A personal hygiene preparation as defined in claim 1, wherein the soap and synthetic detergent comprise from about 30 to about 80 weight percent of the total weight of said preparation, to achieve the consistency of a paste.

4. A personal hygiene preparation as defined in claim 1, wherein the soap and synthetic detergent comprise at least 80 weight percent of the total weight of said preparation, to achieve a consistency moldable into a bar shape.

5. A personal hygiene product as defined in claim 1 wherein the synthetic detergent has a degree of ethoxylation of between 2 and 20.

6. A personal hygiene product as defined in claim 1, wherein said fatty acid and said fatty acid amide are selected from the group consisting of lauric acid, myristic acid, palmitic acid, stearic acid and oleic acid and amides thereof.

* * * * *

UNITED STATES PATENT AND TRADEMARK OFFICE
CERTIFICATE OF CORRECTION

PATENT NO. : 4,865,757
DATED : September 12, 1989
INVENTOR(S) : Shyam Bir Singh-Verma et al.

It is certified that error appears in the above-identified patent and that said Letters Patent is hereby corrected as shown below:

Item [73] should read:

[73] Assignee:

Eau de Cologne- & Parfümerie-Fabrik
Glockengasse No. 4711 gegenüber der
Pferdepost von Ferd. Mülhens,
Cologne, Federal Republic of Germany Signed and Sealed this Nineteenth Day of March, 1991

*Attest:*

HARRY F. MANBECK, JR.

*Attesting Officer*     *Commissioner of Patents and Trademarks*